(12) United States Patent
Gasperino et al.

(10) Patent No.: US 9,638,685 B2
(45) Date of Patent: May 2, 2017

(54) FLOW ASSAY WITH AT LEAST ONE ELECTRICALLY-ACTUATED FLUID FLOW CONTROL VALVE AND RELATED METHODS

(71) Applicant: Tokitae LLC, Bellevue, WA (US)

(72) Inventors: David Gasperino, Lake Forest Park, WA (US); Kevin Paul Flood Nichols, Issaquah, WA (US); Benjamin K. Wilson, Kirkland, WA (US); Ozgur Emek Yildirim, Bellevue, WA (US)

(73) Assignee: TOKITAE LLC, Bellevue, WA (US)

( * ) Notice: Subject to any disclaimer, the term of this patent is extended or adjusted under 35 U.S.C. 154(b) by 406 days.

(21) Appl. No.: 14/490,956

(22) Filed: Sep. 19, 2014

(65) Prior Publication Data

US 2016/0084796 A1 Mar. 24, 2016

(51) Int. Cl.
*G01N 27/447* (2006.01)
*G01N 33/487* (2006.01)
*B01L 3/00* (2006.01)

(52) U.S. Cl.
CPC .. *G01N 33/48721* (2013.01); *B01L 3/502784* (2013.01); *B01L 3/502792* (2013.01); *G01N 27/447* (2013.01)

(58) Field of Classification Search
CPC ............... B01L 33/502794–33/502792; G01N 27/447–27/44795; B01D 57/00–57/02; C02F 1/4696; B81B 1/00–1/008
USPC ................ 204/450–470, 546–550, 600–621, 204/643–645
See application file for complete search history.

(56) References Cited

U.S. PATENT DOCUMENTS

| | | | |
|---|---|---|---|
| 7,216,660 B2 | 5/2007 | Troian et al. | |
| 7,264,337 B2 | 9/2007 | Lee et al. | |
| 8,037,903 B2 | 10/2011 | Wang et al. | |
| 8,356,631 B2 | 1/2013 | Suzuki et al. | |
| 2002/0166592 A1 | 11/2002 | Liu et al. | |
| 2004/0011648 A1* | 1/2004 | Paul | B01D 61/18 204/450 |
| 2010/0159599 A1 | 6/2010 | Song et al. | |
| 2010/0200073 A1* | 8/2010 | Suzuki | B01L 3/502715 137/13 |
| 2011/0185827 A1 | 8/2011 | Asano et al. | |
| 2012/0273053 A1 | 11/2012 | Murphy et al. | |
| 2013/0087459 A1 | 4/2013 | Kong et al. | |
| 2013/0330713 A1 | 12/2013 | Jakubowicz et al. | |

FOREIGN PATENT DOCUMENTS

WO WO 2014/033329 3/2014

OTHER PUBLICATIONS

PCT International Search Report; International App. No. PCT/US2015/049590; Dec. 22, 2015; pp. 1-3.
Esquivel et al. "Microfluidic fuel cells on paper: meeting the power needs of next generation lateral flow devices" Energy and Environmental Science, 2014, 7, 1744-1749.

(Continued)

*Primary Examiner* — Bach Dinh
(74) *Attorney, Agent, or Firm* — Dorsey & Whitney LLP

(57) ABSTRACT

Embodiments disclosed herein are directed to flow assays including at least one electrically-actuated valve configured to control fluid flow. Methods of operating such flow assays are also disclosed.

56 Claims, 7 Drawing Sheets

(56) References Cited

OTHER PUBLICATIONS

Ko et al. "Active Digital Microfluidic Paper Chips with Inkjet-Printed Patterned Electrodes" Advanced Materials, 2014, 26, 2335-2340.
Ren et al. "Automated on-chip droplet dispensing with volume control by electro-wetting actuation and capacitance metering" Sensors and Actuators B 98 (2004) 319-327.
Toley et al. "Tunable-Delay Shunts for Paper Microfluidic Devices" Analytical Chemistry, 2013, 85, 11545-11552.
Yeo et al. "Electrowetting, Applications" Department of Mechanical Engineering, Monash University, 2008, pp. 606-615.

\* cited by examiner

FLOW ASSAY WITH AT LEAST ONE ELECTRICALLY-ACTUATED FLUID FLOW CONTROL VALVE AND RELATED METHODS

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

BACKGROUND

A lateral flow assay ("LFA") can be a paper-based device that detects a presence of an analyte in a sample without the need for costly equipment. LFAs are a common point of care diagnostic tool.

LFAs function by wicking (e.g., capillary action) a sample of interest through a porous membrane (e.g. paper) where chemical reactions can occur in and on the surface of the porous membrane. The LFA can contain a conjugate material therein. Conjugate materials are typically formulated to provide the solvent(s) and reactant(s) necessary to dissolve, react, color, tag, or bond to the suspected analyte in a sample. Thus, if the analyte is present, the conjugate or a component thereof will react with the analyte in the sample. The conjugate can include a taggant or other material configured to provide a visual indication of the presence of the analyte, reacted analyte, or analyte-conjugate complex. Typically, the readout of an LFA is a visual change at some point along a length of the LFA. Many LFAs include an analyte collection material near the distal end of the LFA whereby the analyte and any taggant bonded thereto are bound in large concentration to provide visual indication of a positive or negative result.

LFAs can have limited flow control so that once the liquid enters a LFA, the liquid continues flowing through capillary action at a predetermined rate at least partially governed by the Lucas-Washburn equation. Without flow control, the complexity of chemical reactions that can be carried out in an LFA is limited.

SUMMARY

Embodiments disclosed herein are directed to fluid assays (e.g., LFAs) including an electrically-actuated valve configured to control fluid flow. Methods of operating such fluid assays are also disclosed.

In an embodiment, a flow assay for detecting a presence of an analyte in a sample is disclosed. The flow assay includes at least one hydrophilic porous layer having a proximal end through which the sample can be introduced, a distal end spaced from the proximal end, a first side spaced from a second side, and a gap located between the proximal end and the distal end and located between the first side and the second side. The flow assay includes at least one first hydrophobic layer disposed adjacent to the first side of the at least one hydrophilic porous layer to partially define the gap and at least one second hydrophobic layer disposed adjacent to the second side of the at least one hydrophilic porous layer to partially define the gap. The flow assay further includes a first electrode electrically coupled to the at least one first hydrophobic layer and separated from the at least one hydrophilic porous layer by the at least one first hydrophobic layer and a second electrode electrically coupled to the at least one second hydrophobic layer and separated from the at least one hydrophilic porous layer by the at least one second hydrophobic layer. The flow assay also includes a power source electrically coupled to the first and second electrodes, the power source configured to apply a voltage between the first electrode and the second electrode.

In an embodiment, a method of detecting a presence of an analyte in a sample is disclosed. The method includes providing a flow assay including at least one hydrophilic porous layer having a proximal end through which the sample can be introduced, a distal end spaced from the proximal end, a first side spaced from a second side, and a gap located between the proximal end and the distal end and located between the first side and the second side. The provided flow assay includes at least one first hydrophobic layer disposed adjacent to the first side of the at least one hydrophilic porous layer to partially define the gap and at least one second hydrophobic layer disposed adjacent to the second side of the at least one hydrophilic porous layer to partially define the gap. The provided flow assay also includes a first electrode electrically coupled to the at least one first hydrophobic layer and separated from the at least one hydrophilic porous layer by the at least one first hydrophobic layer, a second electrode electrically coupled to the at least one second hydrophobic layer and separated from the at least one hydrophilic porous layer by the at least one second hydrophobic layer, and a power source electrically coupled to the first and second electrodes. The method includes introducing the sample at the proximal end of the at least one hydrophilic porous layer of the flow assay. The method further includes applying a voltage between the first electrode and the second electrode effective to alter a hydrophobicity of at least one of the at least one first hydrophobic layer or the at least one second hydrophobic layer.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
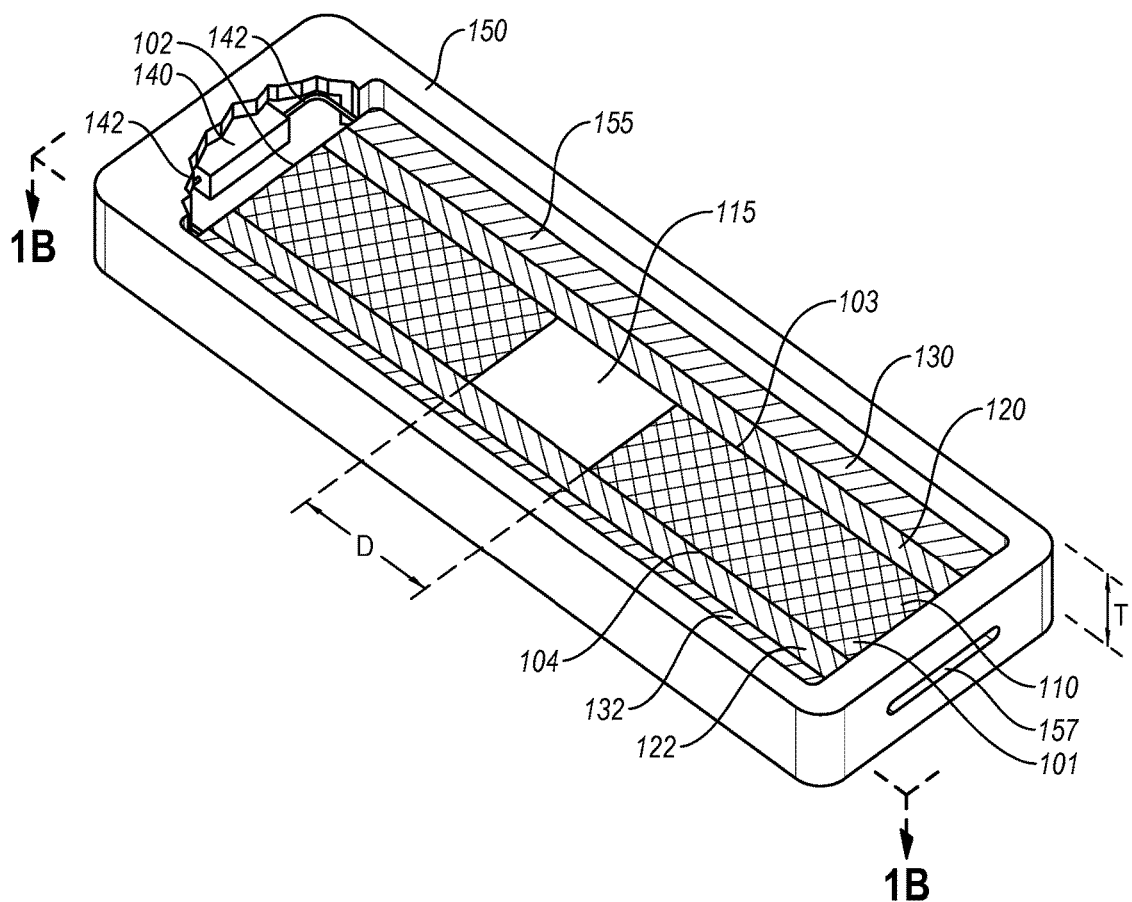
FIG. 1A is an isometric partial cutaway view of a flow assay according to an embodiment.

Embodiments disclosed herein are directed to flow assays (e.g., an LFA) including an electrically-actuated valve configured to control fluid flow. Methods of operating such microfluidic assays are also disclosed.

An LFA can be used to provide point of care testing for a variety of purposes, such as drug tests, pregnancy tests, flu tests, fertility tests, human immunodeficiency virus ("HIV") tests, hepatitis tests, by way of non-limiting example. LFAs function by moving a sample including analyte therein through a length of a capillary bed via capillary action. During capillary transport, the analyte in the sample is exposed to a conjugate material configured to react with the analyte to aid in detection thereof. The conjugate contains a taggant or color molecule. The taggant or color molecule is configured to react with the analyte, reacted analyte molecule, or analyte-conjugate complex and provide a visual indication thereof when concentrated (e.g., bound to an indication strip) in large numbers.

The disclosed embodiments include hydrophilic porous layer that functions as a capillary bed and has a gap therein bordered by hydrophobic material electrically coupled to electrodes, collectively forming an electrically-operated valve. The gap and hydrophobic layers are configured to stop capillary flow of the sample long enough to allow a desired reaction between the analyte in the sample and the conjugate to occur. The sample can be allowed to flow past the gap responsive to application of voltage to the hydrophobic layers. The application of voltage can be controlled via a control system according to desired operational parameters or other criteria.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

Figure 1B:
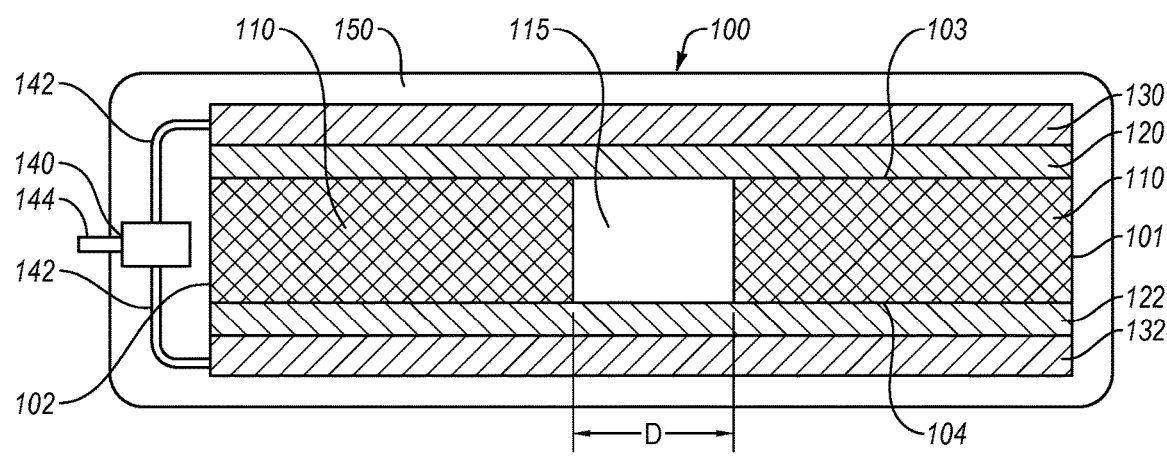
FIG. 1B is a front cross-sectional view of the flow assay of FIG. 1A taken along the line 1B-1B of FIG. 1A.

FIGS. 1A and 1B are illustrations of a flow assay 100 according to an embodiment. FIG. 1A is an isometric cutaway view of the flow assay 100. FIG. 1B is a front cross-sectional view of the flow assay 100 of FIG. 1A taken along the line 1B-1B. The flow assay 100 can be used to determine the presence of one or more specific analytes in a sample. The flow assay 100 can include at least one hydrophilic porous layer 110. The at least one hydrophilic porous layer 110 can include a proximal end 101 spaced from a distal end 102, a first side 103 spaced from a second side 104, and a gap 115 located between the proximal end 101 and the distal end 102 and between the first side 103 and the second side 104. The gap 115 is at least partially defined by the distance "D" between adjacent portions or segments of the at least one hydrophilic porous layer 110.

The flow assay 100 further includes at least one first hydrophobic layer 120 disposed adjacent to the first side 103 of the at least one hydrophilic porous layer 110. The at least one first hydrophobic layer 120 at least partially defines the gap 115. The flow assay 100 also includes at least one second hydrophobic layer 122 disposed adjacent to the second side 104 of the at least one hydrophilic porous layer 110 to at least partially define the gap 115.

The flow assay 100 further includes a first electrode 130 electrically coupled to the at least one first hydrophobic layer 120. The first electrode 130 can be separated from the at least one hydrophilic porous layer 110 by the at least one first hydrophobic layer 120. The flow assay 100 includes a second electrode 132 electrically coupled to the at least one second hydrophobic layer 122. The second electrode 132 can be separated (e.g., spaced) from the hydrophilic porous layer 100 by the at least one second hydrophobic layer 122. The flow assay 100 can include a power source 140 electrically coupled to the first and second electrodes 130 and 132 via electrical connections 142 (e.g., wiring). The power source 140 can be configured to generate, supply, or apply a voltage between the first electrode 130 and the second electrode 132 effective to enable at least the analyte to flow across the gap 115 of the at least one hydrophilic porous layer 110. An actuator 144, electrically coupled with the power source 140, can be configured to initiate and terminate application of voltage. Optionally, the flow assay 100 can include a housing 150 enclosing at least a portion of the hydrophilic porous layer 110, the first and second hydrophobic layers 120 and 122, the first and second electrodes 130 and 132, the power source 140, or the electrical connections 142.

During use, the flow assay 100 can be used to determine or detect the presence of a specific analyte or analytes in a sample. Typical samples can include a liquid containing the analyte (e.g., dispersion, emulsion, etc.) such as diluted or undiluted blood, serum, urine, saliva, mucus, or other samples from a test subject. When exposed to a sample, the at least one hydrophilic porous layer 110 can move the sample through the at least one hydrophilic porous layer 110 via capillary action. The sample can travel through the at least one hydrophilic porous layer 110 until it reaches the gap 115. In an embodiment, the at least one hydrophilic porous layer 110 can further include a conjugate material in at least a portion thereof (e.g., embedded or otherwise dispersed therein). The conjugate material can be formulated to react with a specific analyte (e.g., antigen, molecule, etc.) to yield a specific analyte-conjugate complex or molecule. Typical conjugate materials can include chemical reactants, antibodies, bio-active agents, sugars, salts, taggants, and other materials formulated to ensure satisfactory reaction or bonding between the analyte and one or more conjugate components or indicator components. For example an analyte can be a virus or antigen and a conjugate can contain the antibody to the virus or antigen.

It can be desirable to force the sample and conjugate material to react together for a time longer than the capillary action of the at least one hydrophilic porous layer 110 allows. For example, a given reaction between the conjugate and the analyte in the sample can require 20 minutes to sufficiently develop, whereas the capillary action can carry the analyte past a view area or indicator strip designed to give a visual indication of a product of a reaction in less than 15 minutes, thereby causing a false negative test result.

In the flow assay 100, the sample cannot progress further towards the distal end 102 due to the distance "D" between portions of the at least one hydrophilic porous layer 110 at the gap 115 and the hydrophobic influence of the hydrophobic first and second layers 120 and 122. A voltage can be supplied by the power source 140 to at least one of the first or second electrodes 130 and 132 through the electrical connections 142. The actuator 144 electrically coupled to the power source 140 can control application of the voltage to the first or second electrodes 130 and 132. The applied voltage can act to allow the sample to progress past the gap 115 toward the distal end 102. The voltage can be selectively applied only after a time sufficient to allow for satisfactory extent of, or effective reaction between, the conjugate material and the analyte in the sample. As the conjugate reacts with the sample, a new molecule or complex can be formed. Upon application of the voltage, the complex or new molecule can move toward the distal end 102 through decreased hydrophobicity, induced hydrophilicity, or electro-wetting at one or more of the first or second hydrophobic layers 120, 122 and capillary action within the at least one hydrophilic porous layer 110 proximate to the distal end 102. The application of the voltage can have an electrowetting effect (e.g., lowering the contact angle of a liquid) on the sample, thereby allowing the sample to cross the gap 115.

Without wishing to be bound by theory, it is hypothesized that application of voltage to some hydrophobic materials or electrodes in contact with sample material or conjugate material can result in formation of a layer of less hydrophobic material or at least partially hydrophilic material on the surface of the hydrophobic materials, thereby allowing the sample material to move toward the distal end 102. The layer of less hydrophobic material or at least partially hydrophilic material can reduce the contact angle of the liquid (e.g., sample) sufficient to allow the liquid to cross the gap 115. Thus, the electrically-actuated fluid valves described herein can function at least partially through one or more of electrowetting or formation/coating of at least less hydrophobic material on the surface of the hydrophobic material (or electrodes) in contact with the sample at the gap 115.

In an embodiment, one or more taggants can be disposed in or on the at least one hydrophilic porous layer 110 in the conjugate or proximate to the distal end 102. The one or more taggants can be disposed across the width of the at least one hydrophilic porous layer 110 in one or more lines (e.g., stripe, or strip), dots, blocks, shapes, other designs, or combinations of one or more of the foregoing. The one or more taggants can be formulated to react with a conjugate/analyte complex, conjugate-altered analyte, or analyte molecule to produce a visual indicator of the presence of a conjugate/analyte complex, conjugate altered analyte, or analyte molecule in the sample. Taggants can include latex, gold (e.g., colloidal gold), or other suitable molecules configured to provide a color change or visual indication of a reaction with an analyte when concentrated in large numbers, such as on an indicator portion.

In an embodiment, the flow assay 100 can include an indicator portion or test line. The indicator portion can be a discrete portion of the at least one hydrophilic porous layer 110 that can be proximate to the distal end 102. The indicator portion can include a large concentration of molecules or particles configured to bind to the conjugate/analyte complex, conjugate altered analyte, or analyte molecule including any bound taggant thereon in the sample are located. The indicator portion can include binding molecules, anti-bodies or other particles configured to bind to the conjugate/analyte complex, conjugate altered analyte, or analyte molecule. As larger and larger numbers of the conjugate/analyte complex, conjugate altered analyte, or analyte molecules including bound taggant are bound in the indicator portion, a visual indicator (e.g., color development or change) begins to develop/show therein. The indicator portion can be configured as a strip, stripe, dot, or other shape, as desired.

In an embodiment, the flow assay 100 can include a control portion or control line configured to provide a visual indication that the flow assay operated properly. The control portion can be disposed on a discrete portion of the at least one hydrophilic porous layer 110 at or proximate to the distal end 102 (e.g., closer to the distal end than the indicator portion). The control portion can include a molecule or group of molecules located in a discrete portion of the hydrophilic porous layer 110. The molecules in the control portion can be configured to react with the sample (e.g., any substance in the sample fluid or carried therewith) in order to demonstrate that the flow assay 100 work properly or is complete. The control portion can include a control taggant therein. The control taggant can include latex, gold, or any other particles configured to give a visual indication of their presence upon concentration in large numbers.

In an embodiment, the hydrophilic porous layer 110 can include one or more storage portions. The one or more storage portions can be configured as pads, reservoirs, or portions of the hydrophobic porous layer 110 configured to store a large volume of the sample compared to other portions of the hydrophilic porous layer. For example, the flow assay 100 can include a storage portion near the proximal end 101 configured to hold a large volume of the sample fluid applied to the at least one hydrophilic porous layer 110. The at least one hydrophilic porous layer 110 can then draw the sample therefrom (e.g., the sample travels through the hydrophilic porous layer by capillary action). A similar storage portion can be located near the distal end 102 and can be configured to wick the sample therein, thereby drawing or allowing a sufficient amount of the sample to travel to the distal end 102 to ensure the test provides accurate results.

Any of the flow assays described herein can include one or more taggants, one or more storage portions, an indicator portion, or a control portion.

In an embodiment, the at least one hydrophilic porous layer 110 can include a porous material (e.g., matrix) having a thickness. The at least one hydrophilic porous layer 110 can include, by way of non-limiting example, porous paper, glass fibers (e.g., a glass fiber mat or pad), polymers (e.g., carbonized polymers), or any other material capable of capillary action effective to induce lateral flow therethrough. For example, the at least one hydrophilic porous layer 110 can include nitrocellulose (e.g., a nitrocellulose or cellulose acetate paper or pad).

The at least one hydrophilic porous layer 110 can exhibit a length and width. The length, as measured from the proximal end 101 to the distal end 102, can be at least about 0.25 inches, such as about 0.5 inches to about 5 inches, about 1 inch to about 4 inches, about 1.5 inches to about 3 inches, about 0.5 inches to about 2 inches, about 0.5 inches, about 1 inch, about 1.5 inches, about 2 inches, about 2.5 inches, about 3 inches, or about 4 inches. The width, as measured from the first side 103 to the second side 104, can be at least about 0.125 inches, such as about 0.25 inches to about 1, about 0.375 inches to about 0.75 inches, about 0.5 inches to about 0.625 inches, about 0.25 inches to about 0.75 inches, about 0.25 inches, about 0.5 inches, about 0.625 inches, about 0.75 inches, or about 1 inch. In an embodiment, the at least one hydrophilic porous layer 110 can exhibit a ratio of length to width of about 1:1 or greater, such as about 1:1 to about 20:1, about 2:1 to about 10:1, about 3:1 to about 8:1, about 4:1 to about 6:1, about 2:1, about 3:1, about 4:1, or about 5:1.

In an embodiment, the gap 115 can be defined by the distance D between adjacent portions of the at least one hydrophilic porous layer 110. In an embodiment, the gap 115 can be empty, such as occupied by substantially only air. The adjacent portions of the at least one hydrophilic porous layer 110 can include a proximal portion at the proximal end 101 and a distal portion at the distal end 102 having the gap 115 therebetween. In an embodiment, the gap 115 can extend the entire width of the at least one hydrophilic porous layer 110. Put another way, the gap 115 can extend from the first side 103 to the second side 104. The distance D can be selected based upon one or more of the desired contact angle of the sample, the voltage necessary for the sample to cross the gap 115, or the limitations of how small a gap 115 can be made. The gap 115 can exhibit a distance D, along the length of the flow assay 100, between the proximal portion and the distal portion of about 0.001 inches or more, such as about 0.001 inches to about 1 inch, about 0.005 inches to about 0.5 inches, about 0.01 inches to about 0.05 inches, about 0.02 inches to about 0.04 inches, about 0.02 inches to about 0.3 inches, about 0.05 inches to about 0.5 inches, about 0.025 inches, about 0.05 inches, about 0.1 inches, about 0.25 inches, or about 0.5 inches.

The first and second hydrophobic layers 120 and 122 can include a material configured to reduce in hydrophobicity, plate with a more hydrophilic material, or erode to expose a more hydrophilic material upon application of voltage thereto. For example, the first and second hydrophobic layers 120 and 122 can include, by way of non-limiting example, polymers, silicones, silanes (e.g., trichloro(perfluorooctyl)silane), heptadecafluorodecyltrimethoxysilane, octadecyldimethylchlorosilane, dimethyldichlorosilane, Teflon, or Teflon AF. The first and second hydrophobic layers 120 and 122 can each be made of the same material or each made of a different material.

Each of the first and second electrodes 130 and 132 can include any material suitable to act as an anode or a cathode. For example, the first and second electrodes 130 and 132 can include a metal, a metal alloy, or other suitable electrically conducting compound in the form of a thin film, a plate, a wire, or any other suitable electrical conducting structure. By way of non-limiting example, at least one of the first and second electrodes can include an alkali metal, and alkaline earth metal, a transition metal, a metalloid, an alloy of one or more of the foregoing, a carbon containing material (e.g., graphite or sintered polymer), or an oxide of one or more of the foregoing (e.g., nickel, iron, copper, silver, gold, platinum, palladium, zinc, tin, aluminum, indium, lithium, titanium, germanium, or indium tin oxide). In an embodiment, the first electrode 130 can be configured as an anode and the second electrode 132 can be configured as a cathode. In an embodiment, the first electrode 130 can be configured as a cathode in the second electrode 132 can be configured as an anode. In an embodiment, each of the first electrode 130 and the second electrode 132 can include the same material or a different material. In an embodiment, one or more of the first electrode 130 in the second electrode 132 can include an electrically conductive layer through which the at least one hydrophilic porous layer 110 is viewable (e.g., indium tin oxide).

In an embodiment, at least one of the first or second electrodes 130 and 132 can be configured to chemically react with the sample or conjugate component during application of voltage. In an embodiment, at least one of the first or second electrodes 130 and 132 configured to chemically react with the sample during application of voltage is configured to be coated with a product of the chemical reaction, the product of the chemical reaction being at least partially hydrophilic or less hydrophobic than the original electrode material. In an embodiment, at least one of the first or second electrodes 130 and 132 can be configured to undergo a redox reaction with the sample or a component thereof during application of voltage between the first electrode 130 and the second electrode 132.

In an embodiment, at least one of the first or second hydrophobic layers 120 and 122 can be configured to chemically react with the sample during application of voltage. In an embodiment, at least one of the first or second hydrophobic layers 120, 122 configured to chemically react with the sample during application of voltage is configured to be coated with a product of the chemical reaction, the product of the chemical reaction being at least partially hydrophilic or less hydrophobic than at least one of the first or second hydrophobic layers 120, 122. In an embodiment, at least one of the first or second hydrophobic layers 120, 122 can be configured to undergo a redox reaction with the sample or a component thereof during application of voltage between the first electrode 130 and the second electrode 132.

While depicted as extending the entire length of the at least one hydrophilic porous layer 110, one or more of the first hydrophobic layer 120, the second hydrophobic layer 122, the first electrode 130, or the second electrode 132 can extend less than the length of the at least one hydrophilic porous layer 110. One or more of the first hydrophobic layer 120, the second hydrophobic layer 122, the first electrode 130, or the second electrode 132 can extend a minimum of the distance D at the gap 115 effective to allow the sample to cross the gap 115 upon application of voltage. For example, the first hydrophobic layer 120, the second hydrophobic layer 122, the first electrode 130, and the second electrode 132 can extend a nominal distance past each side of the gap 115 (e.g., overlapping the at least one porous layer 110) effective for the applied voltage to induce the sample to cross the gap 115.

The first and second electrodes 130 and 132 can be electrically coupled to the power source 140 via the electrical connections 142 (e.g., wiring). The power source 140 can include one or more of a battery or a fixed power supply (e.g., hard wiring, plug-in adapter, etc.) configured to selectively supply the specific voltage (e.g., 9 volts) to at least one of the first electrode 130 in the second electrode 132. For example, the power source 140 can supply at least about 1 volt, such as about 1 volt to about 75 volts, about 3 volts to about 30 volts, about 6 volts to about 12 volts, about 1 volt to about 9 volts, about 3 volts, about 6 volts, or about 9 volts. The actuator 144 can be electrically coupled to the battery to control application of voltage between the first and second electrodes 130 and 132. The actuator 144 can be operated by a manual control (e.g., a button, switch, dial, lever, etc.) or an automatic control (e.g., sensor controlled, timer controlled, control electrical circuitry controlled, etc.). The power source 140 can supply power to all or some of the flow assay 100 including any components therein.

As shown in FIG. 1A, the housing 150 can substantially enclose the at least one porous layer 110, the first and second hydrophobic layers 120 and 122, the first and second electrodes 130 and 132, the power source 140, and the electrical connections 142. The actuator 144 (shown in FIG. 1B) can be at least partially enclosed within the housing 150. The housing 150 can include one or more openings 155 (e.g., a cutout, view hole, or window), through which the flow assay can be viewed. The one or more openings can be covered with a transparent material (e.g., glass, plastic, or the like) to allow a user to visibly inspect the flow assay 100. The housing 150 can include a sample opening 157 at or near the proximal end 101, through which a sample can be introduced to the at least one porous layer 110. In an embodiment, the at least one hydrophilic porous layer 110 can protrude out of the sample opening 157 to or beyond the outer periphery of the housing 150.

The housing 150 can have a thickness "T" larger than that of, and sufficient to enclose, the at least one hydrophilic porous layer 110, the first and second hydrophobic layers 120 and 122, the first and second electrodes 130 and 132, the power source 140, the electrical connections 142, and the actuator 144. In an embodiment, the housing 150 can be bisected at a point in the thickness T along the length and width thereof sufficient to form two halves of the housing 150, which can open in a clam shell style (not shown). Such a configuration can allow for replacement or selection and use of different flow assays (e.g., flow assays configured to detect different analytes) within the same housing 150. In an embodiment, the housing 150 can be configured to at least partially enclose additional features disclosed herein below. For example, the housing 150 can be larger at the distal end 102 to accommodate control electrical circuitry.

Figure 2A:
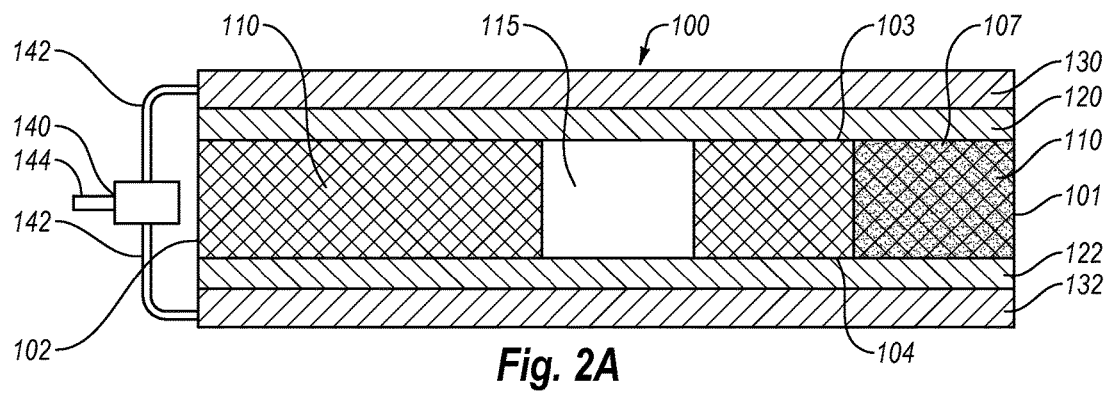
FIGS. 2A-2D are front cross-sectional views of the flow assay of FIG. 1A at different points during use.
Figure 2B:
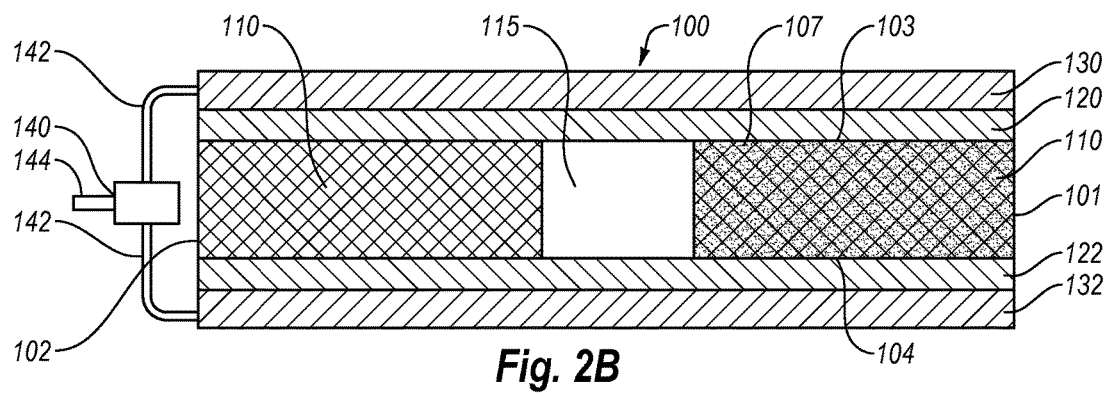
Figure 2C:
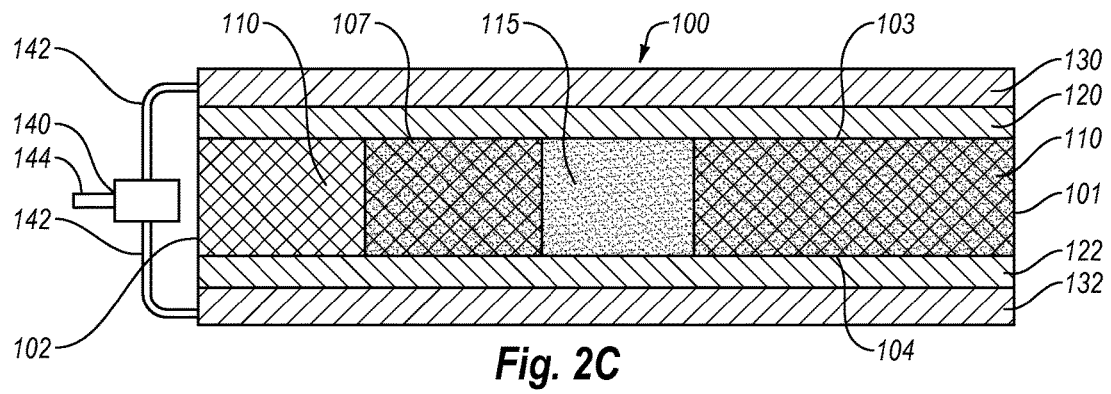

FIGS. 2A-2D are front cross-sectional views of the flow assay 100 of FIGS. 1A and 1B at different points during use. At a point shown in FIG. 2A, a sample 107 can be introduced to the proximal end 101 of the at least one hydrophilic porous layer 110. The sample 107 can be introduced to the proximal end 101 of the at least one hydrophilic porous layer 110 via one or more of immersion, blotting, spotting, or any other suitable sampling technique. The porous material of the at least one hydrophilic porous layer 110 can draw or advance the sample through the length of the at least one hydrophilic porous layer from the proximal end 101 toward the distal end 102 through capillary action (e.g., wicking). At a point shown in FIG. 2B, the at least one hydrophilic porous layer 110 can draw or advance the sample 107 toward the distal 102 until the sample 107 reaches the gap 115. In an embodiment, a conjugate can be disposed within the at least one hydrophilic porous layer 110 near the proximal end 101. The conjugate can be formulated to react with, bond to, or alter the analyte in the sample 107. It can be necessary to allow the reaction of the analyte and the conjugate to progress for a longer period of time than the capillary action of the at least one hydrophilic porous layer 110 can allow. At a point shown in FIG. 2B, the sample can dwell (e.g., not progress past) at the gap 115 without an external force or stimulus for a sufficient amount of time to allow the reaction to take place. As shown in FIG. 2C, a sufficient voltage can be applied between the first and second electrodes 130 and 132, thereby allowing the sample 107, including any reacted analyte or analyte conjugate complex, to progress towards the distal end 102 past the gap 115. Thus, the gap 115, the first and second hydrophobic layers 120 and 122, the first and second electrodes 130 and 132, and the power source 140 can function as a valve mechanism to selectively prevent or allow the sample 107 to move towards the distal end 102 past the gap 115.

Figure 2D:
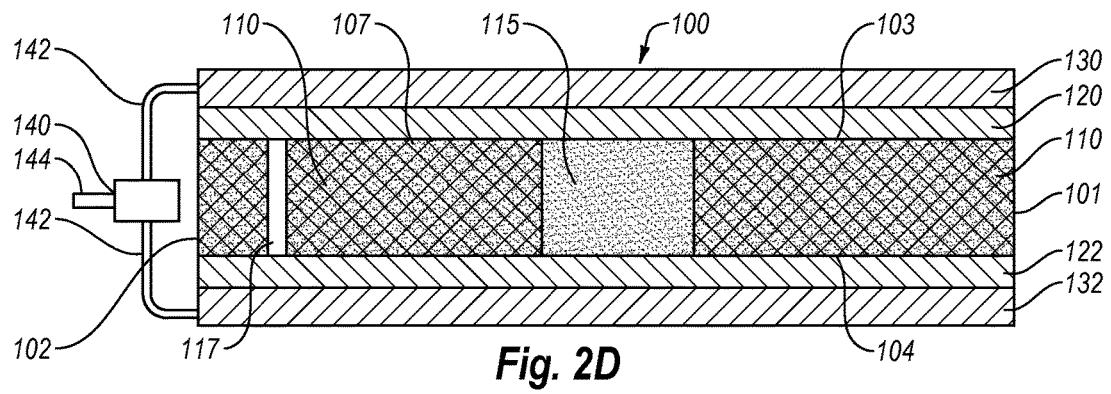

At a point shown in FIG. 2D, the sample can progress within the at least one hydrophilic porous layer 110 to the distal end 102 of the distal portion through capillary action, thereby coming into contact with or passing a indicator portion 117 disposed within the at least one hydrophilic porous layer 110 at or proximate to the distal end 102. The indicator portion 117 can include a plurality of molecules configured react with the product of the reaction between the analyte in the sample and the conjugate (including any taggant therein) or the analyte to give a visual indication of the presence of the analyte in the sample 107. In an embodiment, the taggant can be configured to change the color of the sample liquid or produce a distinctive visual delineation (e.g., stripe, dot, shape, etc.) on the indicator portion 117 of the hydrophilic porous layer 110 when concentrated on the binding molecules therein. The binding molecules can be an antibody or molecule similar or identical to that of the conjugate, such that the analyte bonds to the binding molecules in the indicator portion similarly as to the conjugate, thereby concentrating the analyte and any conjugate (including taggant(s)) thereon in the indicator portion 117.

Figure 3:
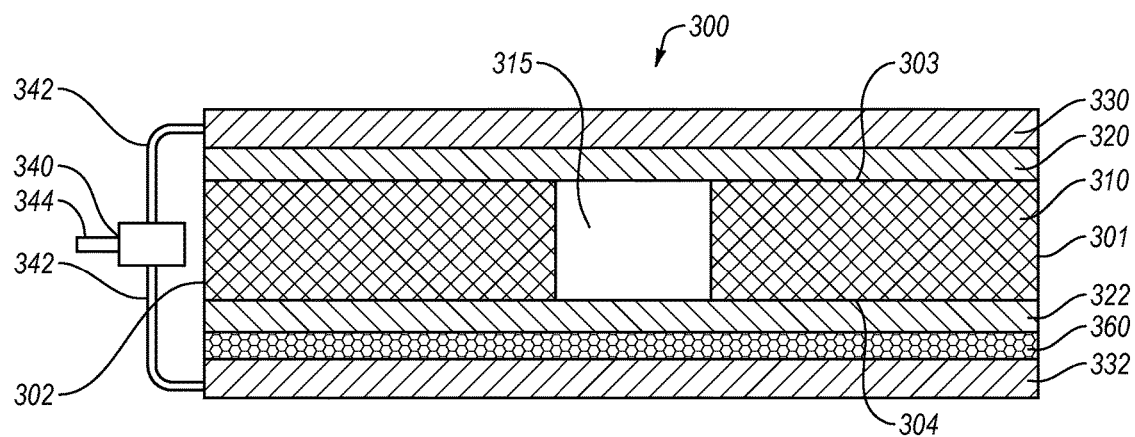
FIG. 3 is a front cross-sectional view of a flow assay according to an embodiment.

FIG. 3 is an illustration of a flow assay according to an embodiment. The flow assay 300 can include at least one hydrophilic porous layer 310 having a proximal end 301, a distal end 302, a first side 303, and second side 304 and gap 315 therebetween substantially similar or identical to the at least one hydrophilic porous layer 110 having a proximal end 101, distal and 102, first side 103, second side 104 and gap 115 therebetween. The flow assay 300 can further include a first hydrophobic layer 320 and a second hydrophobic layer 322 substantially similar or identical to the first hydrophobic layer 120 in the second hydrophobic layer 122. The flow assay 300 can include a first electrode 330 and a second electrode 332 substantially similar or identical to the first and second electrodes 130 and 132, respectively. The flow assay 300 can include a power source 340 electrically coupled to the first and second electrodes 330 and 332 via electrical connections 342, which can be substantially similar or identical to the power source 140 and electrical connections in 142. The power source 340 can be controlled by an actuator 344 substantially similar or identical to the actuator 144.

In the illustrated embodiment, the flow assay 300 can include an insulating layer 360 disposed between the at least one second hydrophobic layer 320 the second electrode 332 as shown in FIG. 3, or between the at least one first hydrophobic layer 320 and the first electrode 330 (not shown). In such embodiments, the insulating layer 360 can act to limit the amount of voltage applied to the sample in the flow assay, thereby controlling the temperature of the sample during use. The insulating layer 360 can include rubber, polymers (e.g., plastics such as polyethylene terephthalate or (e.g., biaxially-oriented polyethylene terephthalate or Mylar, polytetrafluoroethylene or Teflon®) acetate, acrylic, etc.), ceramic materials, glass, or other electrically insulating materials. The at least one insulating layer 360 can have a width sufficient to prevent voltage from passing from between the second hydrophobic layer 322 and the second electrode 332. For example, the at least one insulating layer 360 can exhibit a thickness of about 0.005 inches or more, such as about 0.005 inches to about 0.125 inches, about 0.01 inches to about 0.0625 inches, about 0.025 inches to about 0.05 inches, about 0.01 inches, about 0.025 inches, or about 0.05 inches. Although shown as extending the entire length of the flow assay 300, the insulating layer 360 can extend less than the entire distance of the flow assay 300. For example, the insulating layer 360 can extend only as far as the at least one second hydrophobic layer 322 or the second electrode 332. In an embodiment, an insulating layer 360 can be disposed between the at least one first hydrophobic layer 320 and the first electrode 330 substantially as described above.

Figure 4:
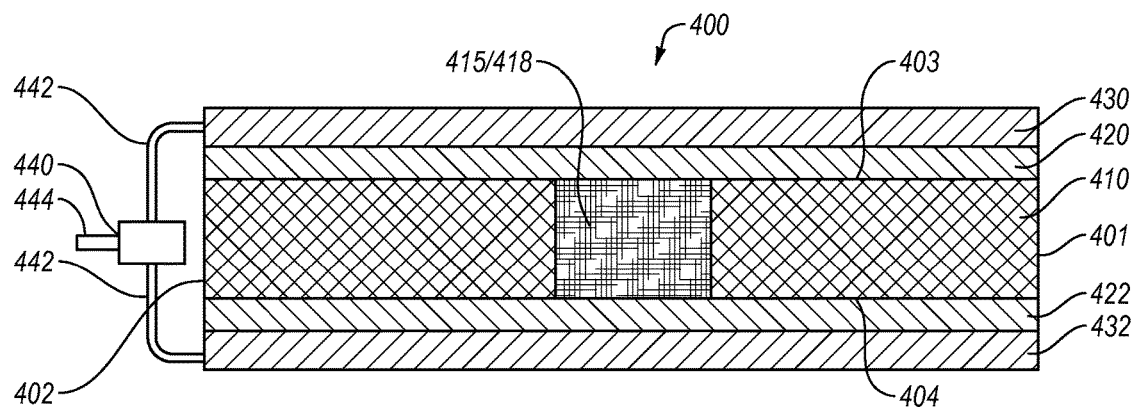
FIG. 4 is a front cross-sectional view of a flow assay according to an embodiment.

FIG. 4 is an illustration of a flow assay according to an embodiment. The flow assay 400 can be substantially similar to the flow assay 100 described herein. The flow assay 400 can include at least one hydrophilic porous layer 410 having a proximal end 401, a distal end 402, a first side 403, and second side 404 and gap 415 therebetween substantially similar or identical to the at least one hydrophilic porous layer 110 having a proximal end 101, distal end 102, first side 103, second side 104 and gap 115 therebetween. The flow assay 400 can include the first hydrophobic layer 420 and a second hydrophobic layer 422 substantially similar or identical to the first hydrophobic layer 120 in the second hydrophobic layer 122. The flow assay 400 can include a first electrode 430 and a second electrode 432 substantially similar or identical to the first and second electrodes 130 and 132, respectively. The flow assay 400 can include a power source 440 electrically connected to the first and second electrodes 430 and 432 via electrical connections 442, which can be substantially similar or identical to the power source 140 and electrical connections in 142. The power source can be controlled by an actuator 444 substantially similar or identical to the actuator 144.

In the illustrated embodiment, a hydrophobic porous material 418 is disposed within the gap 415. The hydrophobic porous material 418 can include any of those materials described above for the at least one first and second hydrophobic layers 120 and 122. In an embodiment, the hydrophobic porous material 418 can include a plurality of fibers (e.g., a matrix, paper, or pad) of any of the hydrophobic materials (e.g., materials used in hydrophobic layers) described herein. In an embodiment, the hydrophobic porous material 418 can be different than the material used in the at least one first and second hydrophobic layers 420 and 422. In an embodiment, the hydrophobic porous material 418 can be the same material used in the at least one first and second hydrophobic layers 420 and 422. The hydrophobic porous material 418 can function to prevent the sample from progressing past the proximal portion of the at least one hydrophilic porous layer 410 until a voltage is applied to one or more of the first and second electrodes 430 and 432. The hydrophobic porous material 418 in within the gap 415 can be configured to reduce in hydrophobicity, become at least partially hydrophilic, or otherwise aid or allow the sample to progress to the distal end 402 of the at least one hydrophilic porous layer 410 upon application of voltage from the power source 440.

The hydrophobic porous material 418 can extend the entire length of the gap 415 from the proximal portion to the distal portion of the at least one hydrophilic porous layer 410. In an embodiment, the hydrophobic porous material 418 can extend less than the entire length of the gap 415, such as about ½ of the length of the gap 415, about one quarter of the length of the gap 415, or about ⅛ of the length of the gap 415. In such embodiments, the hydrophobic porous material 418 can be disposed adjacent to the proximal portion of the at least one hydrophilic porous layer 410, adjacent to the distal portion of the at least one hydrophilic porous layer for 410, centered therebetween, or at a point nearer to one or the proximal portion of the distal portion.

Figure 5:
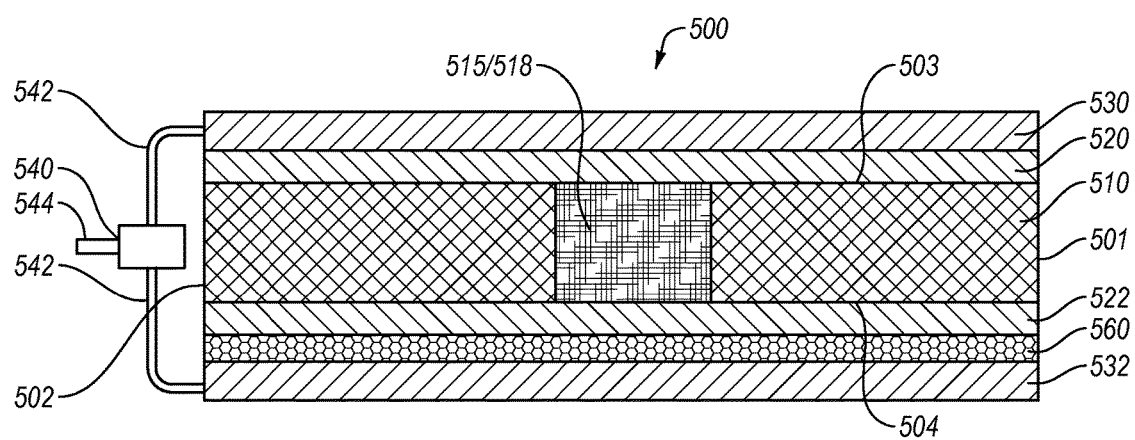
FIG. 5 is a front cross-sectional view of a flow assay according to an embodiment.

FIG. 5 is an illustration of a flow assay according to an embodiment. The flow assay 500 can be substantially similar to the flow assay 100 described herein. The flow assay 500 can include at least one hydrophilic porous layer 510 having a proximal end 501, a distal end 502, a first side 503, and second side 504 and gap 515 therebetween substantially similar or identical to the at least one hydrophilic porous layer 110 having a proximal end 101, distal and 102, first side 103, second side 104 and gap 115 therebetween. The flow assay 500 can include a first hydrophobic layer 520 and a second hydrophobic layer 522 substantially similar or identical to the first hydrophobic layer 120 and the second hydrophobic layer 122. The flow assay 500 can include a first electrode 530 and a second electrode 532 substantially similar or identical to the first and second electrodes 130 and 132, respectively. The flow assay 500 can include a power source 540 electrically connected to the first and second electrodes 530 and 532 via electrical connections 542 which can be substantially similar or identical to the power source 140 an electrical connections in 142. The power source can be controlled by an actuator 544 substantially similar or identical to the actuator 144.

The flow assay 500 can include an insulating layer 560 and a hydrophobic porous material 518 disposed in the gap 515. The insulating layer 560 can be substantially similar or identical to the insulating layer 360 described above, including but not limited any materials, dimensions, positions, or characteristics thereof. The hydrophobic porous material 518 can be substantially similar or identical to that described above with respect to the flow assay 400 in FIG. 4, including but not limited to any materials, dimensions, positions, or characteristics thereof.

Figure 6A:
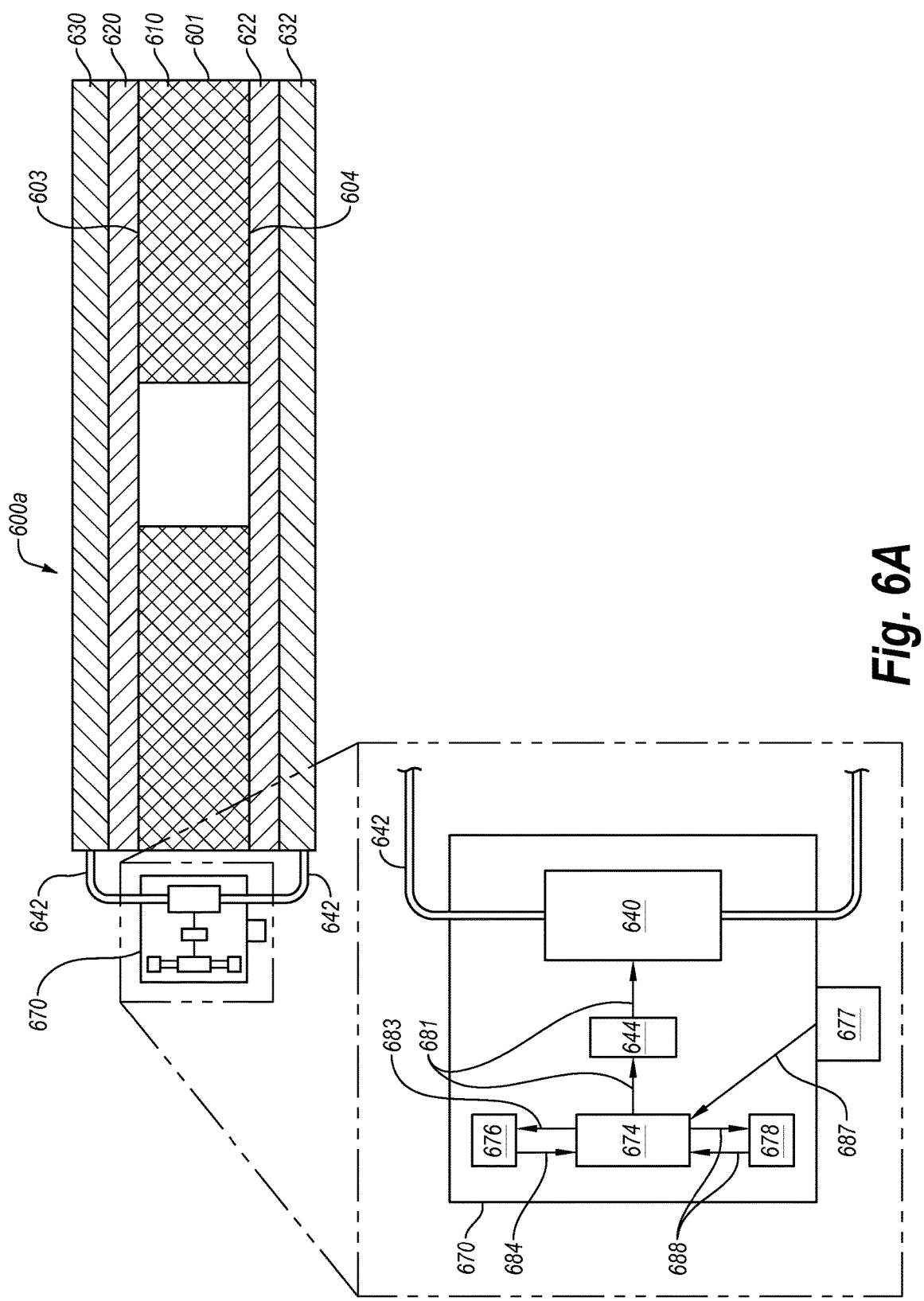
FIG. 6A is a front cross-sectional view of a flow assay according to an embodiment.

FIG. 6A is an illustration of a flow assay according to an embodiment. The flow assay 600 can be substantially similar to the flow assay 100 described herein. The flow assay 600 can include at least one hydrophilic porous layer 610 having a proximal end 601, a distal end 602, a first side 603, and second side 604, and gap 615 therebetween substantially similar or identical to the at least one hydrophilic porous layer 110 having a proximal end 101, distal end 102, first side 103, second side 104, and gap 115 therebetween. The flow assay 600 can include a first hydrophobic layer 620 and a second hydrophobic layer 622 substantially similar or identical to the first hydrophobic layer 120 and the second hydrophobic layer 122. The flow assay 600 can include a first electrode 630 and a second electrode 632 substantially similar or identical to the first and second electrodes 130 and 132, respectively. The flow assay 600 can include a power source 640 electrically coupled to the first and second electrodes 630 and 632 via electrical connections 642 that can be substantially similar or identical to the power source 140 an electrical connections in 142. The power source 640 can be controlled by an actuator 644 substantially similar or identical to the actuator 144.

The flow assay 600 can include a control system 670 including control electrical circuitry 674 (e.g., one or more logic circuits). The control electrical circuitry 674 can be operably coupled to and configured to selectively direct one or more actuators 644 via one or more activation or actuation signals 681 to cause the power source 640 to supply or terminate voltage to the first or second electrodes 630 and 632. The control electrical circuitry 674 can selectively control the amount of voltage applied or the duration of application of voltage based on or responsive to selected operational parameters. The control electrical circuitry 674 can be operably connected to the power source 640 (e.g., via the actuator or directly).

The control system 670 can include a timer 676 operably coupled to and controlled by the control electrical circuitry 674. The timer 676 can be configured to begin timing responsive to a start signal 683 and provide a timer signal 684 to the control electrical circuitry 674 after a specific duration has passed after the start signal 683. The timer signal 684 can trigger the control electrical circuitry 674 to provide (e.g., relay) the activation signal 681 to the actuator 644, thereby directing the power source 640 to provide voltage to one or more of the first or second electrodes 632, 634. The duration required for the timer signal 684 can be at least partially based upon on or more of the desired reaction time of the suspected analyte in a sample and the conjugate used in the at least one hydrophilic porous layer 610, one or more dimensions of the at least one hydrophilic porous layer 610, the material make-up of the at least one hydrophilic porous layer 610, or the sample type. In an embodiment, the start signal 683 can be triggered by user input at a user interface 677, a button, a switch, a computer command, or by control electrical circuitry responsive to a detection or feedback signal from a sensor. User interface 677 can include, by way of non-limiting example, a keypad, monitor, touch screen, voice command recognition, or combinations thereof that is operably coupled to the control electrical circuitry and which can generate a user input signal 687 to the control electrical circuitry.

As will be discussed in more detail below, instructions that the control electrical circuitry 674 of the control system 670 employs for directing and controlling the operation of the flow assay 600 including one or more of the timer 676, the one or more actuators 644, the power source 640, or one or more sensors can be pre-programmed in the control electrical circuitry 674, or programmed at the user interface 677 by the user or other person such as a medical professional like a doctor, a nurse, lab technician, etc. For example, the programming of the control electrical circuitry 674 can be effected via at least one of software, hardware, firmware, programmable logical devices, or other technique for controlling the operation of the flow assay 600. The instructions can be stored on a memory 678 operably coupled to and accessible by the control electrical circuitry 674. The user interface 677 can be used to input data into or access the memory 678. The power source 640 can supply power to all or some of the flow assay 600*a* including any components therein.

Figure 6B:
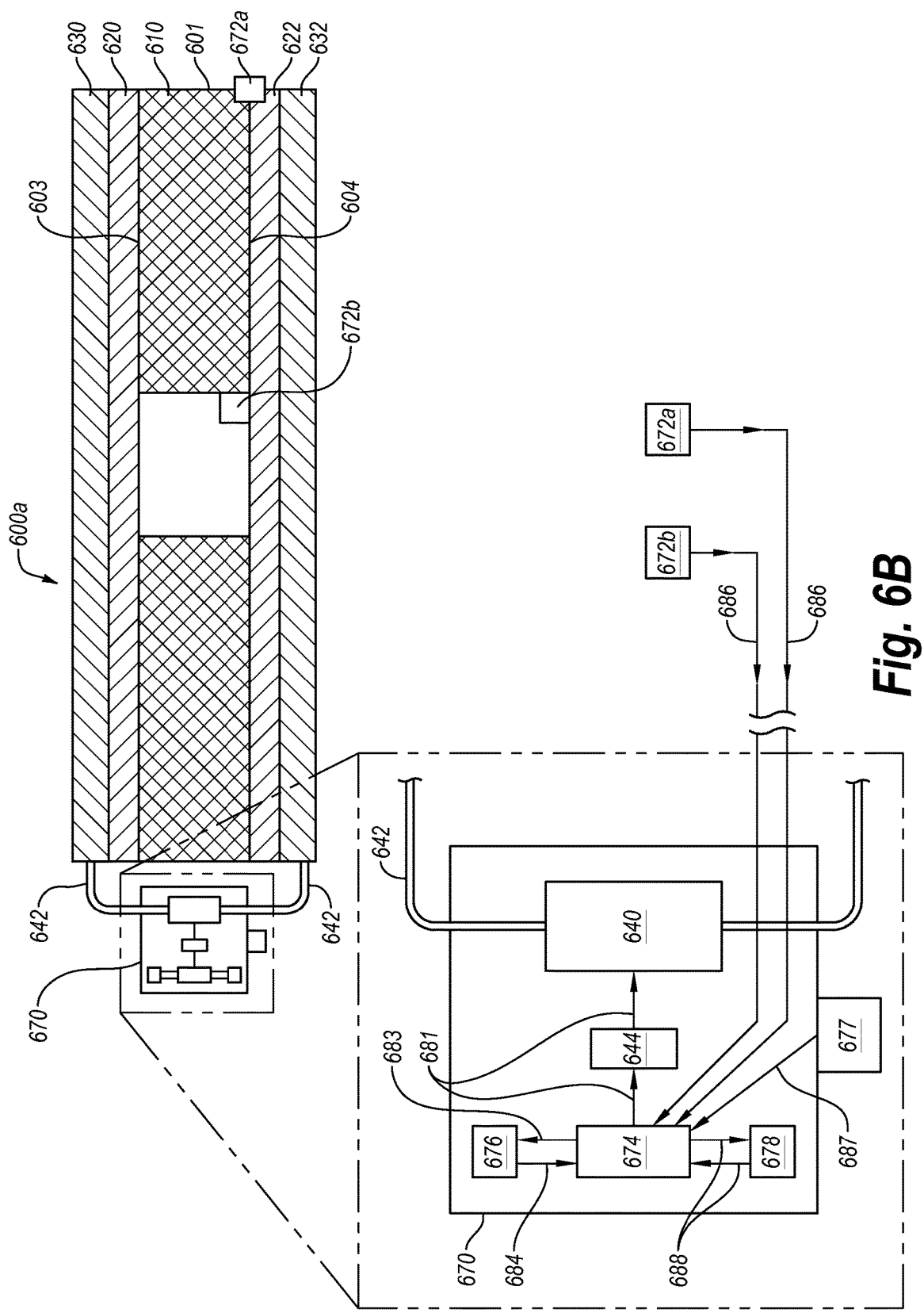
FIG. 6B is a front cross-sectional view of a flow assay according to an embodiment.

The flow assay 600 depicted in FIG. 6B can be substantially similar or identical to the flow assay depicted in FIG. 6A, and can further include one or more sensors 672*a* and 672*b* operably connected (e.g., by wiring or by wireless connection) to the control electrical circuitry 674. The one or more sensors 672*a* and 672*b* can be configured to provide detection or feedback signals 676 to the control electrical circuitry 674. The one or more sensors 672*a* and 672*b* can be configured to detect, by way of non-limiting example, the presence of a sample, the pH in the sample, the resistance in the sample, or any other suitable criteria. For example, one or more of the sensors 672*a* and 672*b* can include one of a pH meter, a resistance meter, or any other suitable sensor. The control system 670 including control electrical circuitry 674 can be configured to selectively direct one or more actuators 644 via one or more activation or actuation signals 681 to cause the power source 640 to supply voltage to the first or second electrodes 630 and 632 responsive to feedback from one or more sensors 672*a* or 672*b*. The timer signal 684, user input signal 687 (e.g., user indication to immediately apply voltage), or sensor feedback signal(s) 686 can be collectively or individually referred to as activation signal(s) 681. The one or more activation signals 681 can be delivered to the control electrical circuitry 674 which can relay the activation signal 681 to the actuator 644. The feedback signal(s) 686 from the sensors 672*a* and 672*b* can include information regarding one or more of detection of the presence of a sample, detection of a specific pH, detection of a specific resistance in the sample, no detection of any selected indicia, or any other suitable criteria. In an embodiment, housing (not shown) similar or identical to housing 150, can at least partially enclose one or more portions of the control system 670.

For example, as shown in FIG. 6B, the sensor 672*a* can be positioned at or proximate to the proximal end 601 of the flow assay 600. The sensor 672*a* can be a resistance sensor, whereby, upon exposure to a liquid in the sample, either directly or as transmitted through the at least one hydrophilic porous layer, the sensor 672*a* can detect a change in resistance due to the presence of the sample and send feedback to the control electrical circuitry 674. In an embodiment, upon receiving feedback from the sensor 672*a*, the control electrical circuitry 674 can selectively generate a start signal 683 to the timer 676 which can in turn generate a timer signal 684 to the control electrical circuitry 674 upon expiration of a selected time period. The control electrical circuitry 674 can then send the activation signal 681 to the actuator 644 to apply a selected voltage, thereby allowing the sample including any analyte therein or any analyte-conjugate complex to cross the gap 615. In an embodiment, the amount or duration of voltage can be adjusted by the control electrical circuitry responsive to feedback from the one or more sensors 672*a* or 672*b*. For example, if a pH meter is used for sensor 672*a* or 672*b*, the control electrical circuitry can send an activation signal 681 to the actuator to apply higher or lower voltage or for a shorter or longer duration based on the level of the detected pH as communicated in the feedback signal 686.

In an embodiment, the sensor 672*b* can be positioned at, within, or proximate to the gap 615. The sensor 672*b* can be a pH sensor configured to sense a pH of the sample, or a resistance sensor configured to determine a change in resistance upon contacting the sample. The sensor 672*b* positioned at, within, or proximate to the gap 615 can send feedback to the control electrical circuitry 674 indicating that the sample has reached the gap 615 or is at a certain pH which can then trigger the start signal 683 to the timer 676. The timer 676 can send the timer signal 684 to the control electrical circuitry 674, which can send the activation signal 681 to the actuator 644 to apply voltage to the first and second electrodes 630 and 632 thereby allowing the sample to cross the gap 615.

In an embodiment, the sensor 672*a* and a sensor 672*b* can be configured as different sensor types or the same sensor type. For example, the sensor 672*a* can be positioned proximate to the proximal end 601 and the sensor 672*b* can be positioned proximate to the gap 615, with both sensors contacting the at least one hydrophobic porous layer 610. Both of the sensors 672*a* and 672*b* can be pH sensors, and as the sample is moved through the at least one hydrophobic layer 610 towards the gap 615, the sensor 672*a* can detect a first pH and sensor 672*b* can detect a second pH. The detected pHs can be sent to the control electrical circuitry 674 as feedback and the extent of a reaction between the sample and the conjugate material within the at least one hydrophobic layer 610 can be determined responsive to the feedback. In an embodiment, two or more sensors can be used in a flow assay. In an embodiment, one or more of the sensors 672*a* and 672*b* can be positioned anywhere along the length of the flow assay 600. In an embodiment, the sensors 672*a* and 672*b* can be modular, or able to be replaced, with the same sensor or replaced with another type of sensor. In an embodiment, the sensor 672*a* can be a resistance sensor configured to send feedback upon detection of a sample to start a timer and the sensor 672*b* can be a pH sensor configured to detect the selected pH of the sample, either one of which can provide the feedback to trigger application of voltage.

The control system 670 can further include a memory 678 operably coupled with the control electrical circuitry 674.

The memory 678 can be programmed with and store instructions for controlling the operation of the flow assay 600.

The memory 678 can be programmed with and store operational parameters such as but not limited to timer durations, voltage application, voltage termination, voltage amount, and voltage duration. Operational parameters can be selected based at least partially on one or more of other operational parameters, or further criteria such as but not limited to the sample type, the hydrophilic porous layer material, conjugate type, suspected analyte type, electrode material, hydrophobic layer material, dimensions of one or more of hydrophilic porous layers, electrodes, hydrophobic layers.

The above criteria for determining the operational parameters can be stored in the memory 678. The control electrical circuitry 674 or memory 678 can be programmed via the user interface 677. The memory 678 can be programmed with instructions for operation, operational parameters, or instructions for determining operational parameters based on any of the above listed criteria via a user interface 677. The memory 678 can be accessed 688 (e.g., access, input, store, or retrieve information in or from) by the control electrical circuitry 674 to compare, determine, or otherwise use the instructions for operation, operational parameters, instructions for determining operational parameters or user input stored therein. Using the information stored in the memory 678, the control electrical circuitry 674 can determine and control the timer 676 or send/relay an activation signal 681 to the actuator 644. Such a determinations, controls, and or signals can be based upon and responsive to one or more of instructions for operation, operational parameters, instructions for determining operational parameters, receipt of timer signal, or feedback from the sensors.

For example, the user can input one or more of the dimensions and material of the at least one hydrophilic porous layer 610, the gap distance D, the material in the gap 615, the conjugate material, or the suspected analyte into the memory 678. The control electrical circuitry 674 can select, adjust, or determine the timer duration, voltage amount, or voltage duration based on the information in the memory 678 or input by the user at the user interface 677. In an embodiment, the control electrical circuitry can access 688 (e.g., access, input, store, or retrieve information in or from) the memory 678 to determine or adjust one or more of instructions for operation, instructions for determining operational parameters, timer duration, voltage amount, or voltage duration. Such determination and adjustment can be responsive to one or more of sensor feedback signals 686, timer signals 684, or activation signals 681, criteria in the memory 678, or user input signals 687.

In an embodiment, a housing (not shown) similar or identical to housing 150, can at least partially enclose one or more portions of the control system 670 and one or more of the first and second sensors 672a and 672b. Any of the disclosed embodiments herein can include one or more of the control system 670, at least one sensor 672a and 672b, the control electrical circuitry 674, the timer 676, the user interface 677, or the memory 678 as described above.

Figure 7:
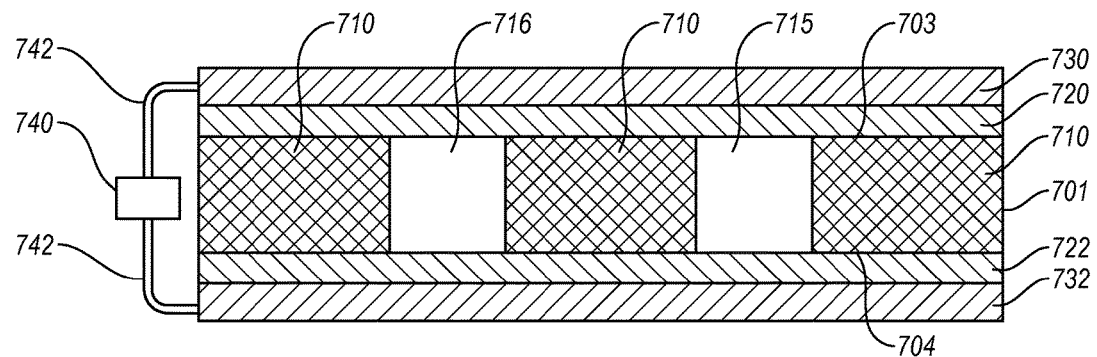
FIG. 7 is front cross-sectional view of a flow assay according to an embodiment.

FIG. 7 is an illustration of a flow assay according to an embodiment. The flow assay 700 can include at least one hydrophilic porous layer 710 having a proximal end 701, a distal end 702, a first side 703, and second side 704 substantially similar or identical to the at least one hydrophilic porous layer 110 having the proximal end 101, distal end 102, first side 103, and second side 104. The flow assay 700 can include a first hydrophobic layer 720 and a second hydrophobic layer 722 substantially similar or identical to the first hydrophobic layer 120 and the second hydrophobic layer 122. The flow assay 700 can include a first electrode 730 and a second electrode 732 substantially similar or identical to the first and second electrodes 130 and 132, respectively. The flow assay 700 can include a power source 740 electrically coupled to the first and second electrodes 730 and 732 via electrical connections 742 which can be substantially similar or identical to the power source 140 an electrical connections in 142. The power source can be controlled by an actuator 744 substantially similar or identical to the actuator 144. The flow assay can include a control system (not shown) or one or more sensors (not shown) as described herein.

The hydrophilic porous layer 710 can include one or more gaps therein, such as a first gap 715 and a second gap 716 spaced therefrom. The first gap 715 can be located proximate to the proximal end 701 and the second gap 716 can be located proximate to the distal end 702. Thus, the hydrophilic porous layer 710 can include a proximal portion at the proximal end 701, a distal portion near the distal end 702, and a medial portion therebetween, with the medial portion being isolated from the proximal and distal portions by the first and second gaps 715 and 716. The first and second electrodes 730 and 732 can function and be used to allow the sample and any materials therein to progress past the individual first and second gaps 715 and 716 in a similar or identical manner as any electrodes and gaps described herein In an embodiment, a first conjugate can be located in the proximal portion of the at least one hydrophilic porous layer 710 and a second conjugate can be located within the medial portion of the at least one hydrophilic porous layer 710. It can be desirable to allow the sample (including any analyte therein) to react with the first conjugate for a selected time to allow sufficient or complete reaction thereof prior to applying voltage to the first and second electrodes 730 and 732 sufficient to allow the sample, reacted analyte, and or analyte-first conjugate complex to progress to the medial portion of the at least one hydrophilic porous layer 710. At the medial portion, the sample, reacted analyte, and or analyte-first conjugate complex can come into contact and react with the second conjugate for a time sufficient to allow satisfactory or complete reaction therebetween. After such time, voltage can be applied to the first and second electrodes 730 and 732 sufficient to allow the sample including any analyte, reacted analyte, or analyte-first and second conjugate complex to flow past the gap 716 to the distal portion of the at least one hydrophilic porous layer 710. An indicator portion (not shown) can be disposed in the distal portion of the at least one hydrophilic porous layer 710 at or proximate to the distal end 702. The indicator portion can include molecules configured to bind the analyte (including any conjugate and taggant bonded thereto) thereon. The conjugate can contain a taggant configured to provide a visual indication of the analyte, the reacted analyte, the analyte-first and second conjugate complex or combinations of one or more of the foregoing upon concentration in large numbers at the indication portion or strip.

In an embodiment, one or more of the at least one first hydrophobic layer 720, at least one second hydrophobic layers 722, or the first and second electrodes 730 and 732 can be broken (e.g., have a gap therein) between the proximal and distal ends of the medial portion of the at least one hydrophilic porous layer 710. The first and second electrodes 730 and 732 can be electrically coupled to the power source 740 on both sides of the gap therein. In operation, voltage can be selectively applied to the at least one first and second hydrophobic layers 720 and 722 and the first and second electrodes 730 and 732 only near the gap 715 or only near the gap 716.

Figure 8:
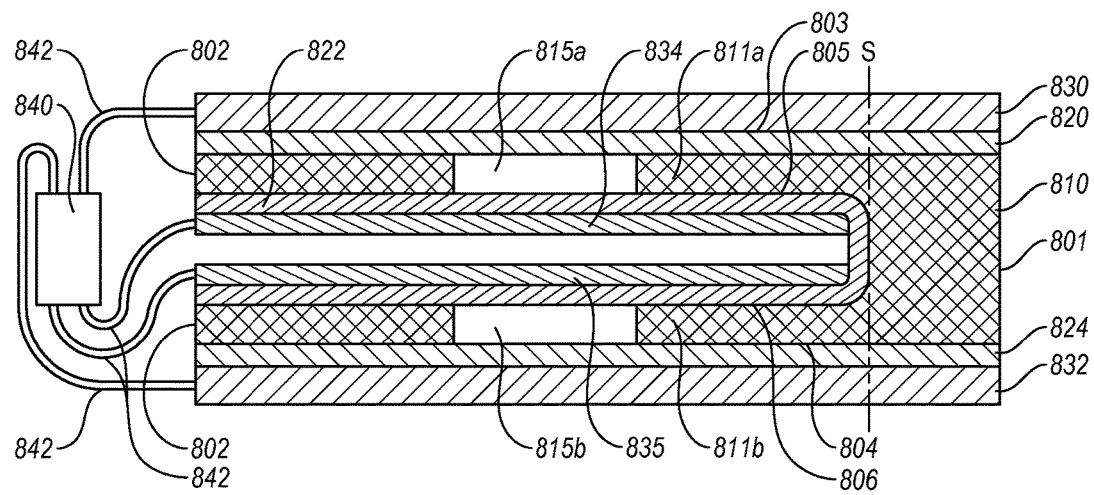
FIG. 8 is a front cross-sectional view of a flow assay according to an embodiment.

FIG. 8 is an illustration of a flow assay according to an embodiment. In an embodiment, the flow assay 800 can split into two or more branches, each configured to individually test for an analyte substantially as described herein. Portions or components of the flow assay 800 can be substantially similar to portions or component of any flow assay described herein.

The flow assay 800 can include at least one hydrophilic porous layer 810 having a proximal end 801, a distal end 802, a first branch 811a and a second branch 811b on the distal end 801 side of the reference line S. The first and second branches 811a and 811b of the at least one hydrophilic porous layer 810 are separated by a space therebetween extending from a point intermediate to the proximal and distal ends 801 and 802 (marked by the reference line S) to the distal end 802. The at least one hydrophilic porous layer 810 can include a first side 803, a second side 804, in interior first side 805 generally opposite and generally parallel to the first side 802, and an interior second side 806 generally opposite and generally parallel to the second side 804. The split or division between the branches 811a and 811b can allow for substantially simultaneous capillary flow of the same sample material into both branches 811a and 811b. In an embodiment, each branch 811a and 811b can be configured to detect the presence of the same analyte or a different analyte. In an embodiment, each branch 811a or 811b can have the same or different conjugate materials therein. In an embodiment, each conjugate in the branch 811a or 811b can have the same or different taggants therein. In an embodiment, each branch 811a or 811b can have the same or different indicator portions therein. The flow assay 800 can include any conjugate or taggant described herein.

The first and second branches 811a and 811b of the at least one hydrophobic layer 810 can each have a gap 815a and 815b therein, respectively. The gaps 815a and 815b can be configured substantially similar or identical to any gap described herein. For example, the first and second gaps can have any gap distance D, any material therein, or any other property described for a gap herein. The first and second gaps 815a and 815b can be substantially similar or identical or can be different, such as but not limited to dimensions or materials therein.

The flow assay can include one or more first hydrophobic layer 820 bound to the at least one hydrophilic porous layer along the first side 802. The flow assay can include one or more second hydrophobic layer 822 bound to the at least one hydrophilic porous layer along the second side 804. The flow assay can include one or more third hydrophobic layer 824 bound to the at least one hydrophilic porous layer 810 along the interior first side 805 or the interior second side 806. The third hydrophobic layer 824 can extend from the interior first side 805 at the distal end 802 around the split in the branches 811a and 811b at the reference line S to the interior second side 806 to the distal end of least one hydrophilic porous layer 810. The first, second, and third hydrophobic layers 820, 822 and 823 can include substantially any of the same materials, dimensions or properties of any of the hydrophobic layers described herein.

The flow assay 800 can include a first electrode 830 attached to and extending along the length of the first hydrophobic layer 820, and a second electrode 832 attached to and extending along length of the second hydrophobic layer 822. The first and second electrodes 830 and 832 can be separated from the at least one hydrophilic porous layer 810 by the first and second hydrophobic layers 820 and 822, respectively. The flow assay 800 can include an interior first electrode 834 attached to and extending along the length of the third hydrophobic layer 824 on the first branch 811a (generally opposite the first electrode 830), and an interior second electrode 836 attached to and extending along the length of the third hydrophobic layer 824 on the first branch 812a (generally opposite the first electrode 832). The interior first and second electrodes 834 and 836 can be separated from the at least one hydrophilic porous layer 810 by third hydrophobic layer 824. The first electrode 830 and the interior first electrode 834, and the second electrode 832 and the interior second electrode 836 can be individually electrically connected to a power source 840 by electrical connections 842. The first and second electrodes 830 and 832 and the interior first and second electrodes 834 and 836 can be substantially similar or identical to any of the electrodes described herein, including electrode material, anode or cathode status, and dimensions.

During use, the first electrode 830 and the first interior electrode 834 of the first branch 811a can be used to apply a voltage at the same time or at a different time as the (generally opposite the first electrode 830) the second electrode 832 and the second interior electrode 836 of the second branch 811b. For example, two different conjugates can be used in flow assay 800, a first conjugate in the first branch 811a and a second conjugate in the second branch 811b. The first and second conjugates can be configured to react with the same analyte in a sample by a different means or react with different analytes in the same sample. It can be necessary for the samples to remain at the gaps 815a and 815b for different times. Thus, voltage can be applied to the first electrode 830 and the first interior electrode 834 of the first branch 811a at a different time than voltage is applied to the second electrode 832 and the second interior electrode 836 of the second branch 811b.

Although shown as substantially the same, the branches 811a and 811b can have one or more of different dimensions (e.g., length, width, or thickness), different materials therein, different conjugates, different taggants, different voltages amounts or durations applied, or different sized gaps.

In an embodiment, the flow assay 800 can include a housing substantially similar to any housing described herein. In an embodiment, the flow assay 800 can include a control system including one or more of control electrical circuitry, a timer, one or more sensors, a user interface, or memory, each being substantially similar or identical to any described herein. For example, the flow assay 800 can include at least one sensor in each of the branches 811a and 811b operably coupled with the control electrical circuitry to selectively control the application of voltage in each of the branches 811a and 811b responsive to the sensors. In an embodiment, the flow assay 800 can include one or more timers, configured to time each branch 811a and 811b separately and provide a timer signal to the control electrical circuitry.

Figure 9:
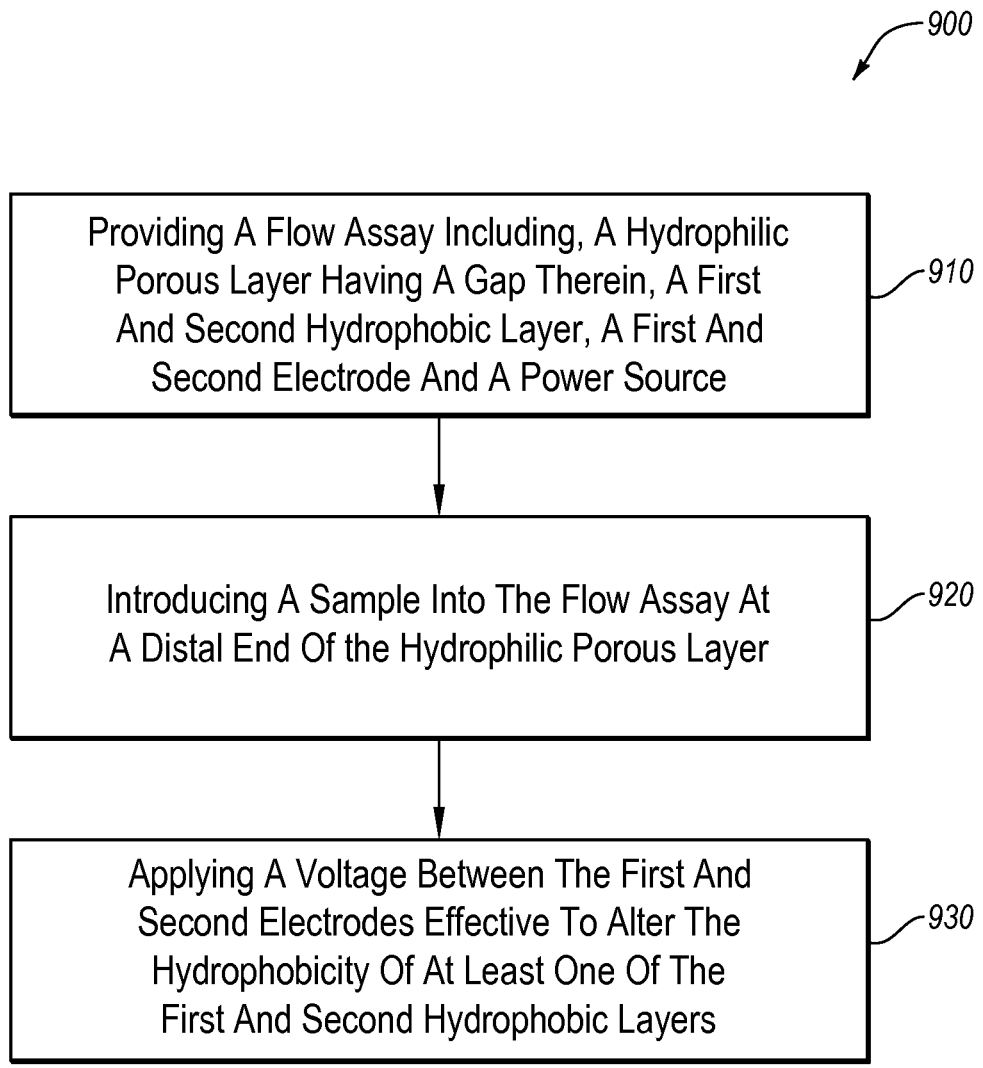
FIG. 9 is a schematic of a method of using a flow assay according to an embodiment.

FIG. 9 is a flow diagram of an embodiment of a method 900 of detecting the presence of an analyte in a sample. The method can include an act 910 of providing a flow assay. The flow assay can be substantially similar to any flow assay described herein. For example, the flow assay can include at least one hydrophilic porous layer having a proximal end through which the sample can be introduced, a distal end spaced from the proximal end, a first side spaced from a second side, and a gap located between the proximal end and the distal end and located between the first side and the second side. The flow assay can include at least one first hydrophobic layer disposed adjacent to the first side of the at least one hydrophilic porous layer to partially define the gap and at least one second hydrophobic layer disposed adjacent to the second side of the at least one hydrophilic porous layer to partially define the gap. The flow assay can further include a first electrode electrically coupled to the at least one first hydrophobic layer and separated from the at least one hydrophilic porous layer by the at least one first hydrophobic layer, and a second electrode electrically coupled to the at least one second hydrophobic layer and separated from the at least one hydrophilic porous layer by the at least one second hydrophobic layer.

The method 900 can include an act 920 of introducing the sample at the distal end of the at least one hydrophilic porous layer of the flow assay. The act 920 can include immersing, spotting, dotting, blotting, dropping, pipetting or any other means of applying a liquid sample to a porous substance.

The method 900 can further include an act of 930 of applying a voltage between the first electrode and the second electrode effective to alter a hydrophobicity of at least one of the at least one first hydrophobic layer or the at least one second hydrophobic layer. The act 930 can include applying or using a voltage effective to allow one or more of the analyte, analyte-conjugate complex, reacted analyte, or the sample in the at least one hydrophilic porous layer to progress past the gap therein so the determination of the presence of the analyte in the sample can be made. In an embodiment, the act 930 can include applying or using a voltage effective to enable a chemical reaction between the sample and at least one of the first electrode, the second electrode, the first hydrophobic layer, or the second hydrophobic layer sufficient to form a reaction product on the surface of the first electrode, the second electrode, the first hydrophobic layer, or the second hydrophobic layer.

In an embodiment, the act 930 can include selectively applying (e.g., initiating, terminating, amount, or duration) of the voltage after a predetermined time period at least partially based on at least one of the type of suspected analyte, sample type, the type of hydrophilic porous material using in the at least one hydrophilic porous layer, one or more dimensions of the at least one hydrophilic porous layer, the type of conjugate used in the hydrophilic porous layer, or any other suitable criteria disclosed herein. In an embodiment, the length of time the voltage is applied can be used to at least partially determine the amount of voltage used.

In an embodiment, the method 900 can include the act of allowing the sample to flow to the gap for a predetermined amount of time prior to applying the voltage. In an embodiment, the method 900 can include the act of allowing the sample to flow across the gap (while the voltage is supplied) for a predetermined amount of time prior to terminating the application of voltage. In an embodiment, the predetermined amount of time can be selected based upon one or more of the time it takes for the suspected analyte to react with the conjugate to a satisfactory degree, the dimensions of the at least one hydrophilic porous layer, the material type of the at least one hydrophilic porous layer, the analyte, the sample, the conjugate, or any other suitable criteria described herein. In an embodiment, the predetermined amount of time can be 5 seconds or more, such as about 5 seconds to about 1 hour, about 30 seconds to about 45 minutes, about 1 minute to about 30 minutes, about 5 minutes to about 20 minutes, about 10 minutes to about 30 minutes, about 5 minutes, about 10 minutes about, about 15 minutes, about 20 minutes, about 30 minutes, or about 1 hour.

In an embodiment, the material used to form the at least one hydrophilic porous layer can be selected at least partially based upon one or more of suspected analyte or analyte type, sample type, one or more dimensions of the gap, presence and type of material in the gap, required conjugate, amount of voltage needed for the sample to cross the gap, or the dimensions of the at least one hydrophilic porous layer (e.g., length, thickness, or width).

In an embodiment, the user interface can be used to direct the control electrical circuitry of the control system to provide or relay an activation signal to the actuator or directly to the power supply to a selected time period after the user direction is input into the user interface. In an embodiment, the user can input the selected time period (e.g., the selected delay time) such as any time period descried herein. In an embodiment, the user can input the selected voltage amount, such as any voltage amount described herein.

In an embodiment, the method can include programming operational instructions, programming operational parameters, inputting criteria, or programming instructions for determining operational parameters into the memory 678 via the user interface 677. Thus, in an embodiment, applying a voltage between the first and second electrodes takes place at least partly according to a pre-programmed operational instruction, parameter or criteria. In an embodiment, the user interface can be used to input, by way of non-limiting example, the sample type, suspected analyte being detected, one or more dimensions of the at least one hydrophilic porous layer, one or more dimensions of the gap, presence and type of material in the gap, type of hydrophobic material used in the at least one first and second hydrophobic layers, or any other criteria. In an embodiment, the operational parameters can be input or selected based on one or more of the time it takes for the suspected analyte to react with the conjugate to a satisfactory degree, one or more of the dimensions of the at least one hydrophilic porous layer, one or more of the dimensions of the gap, the material type of the at least one hydrophilic porous layer, the analyte or type thereof, the sample or type thereof, the conjugate or type thereof, presence or type of material in the gap, type of hydrophobic material used in the hydrophobic material layers, or any other suitable criteria described herein. In an embodiment, the control electrical circuitry can determine the operational parameters at least partially based on one or more of the other operational parameters or one or more of the criteria listed above. In an embodiment, the control electrical circuitry can direct a signal to one or more of the timer, actuator, or power supply to carry out one of the operational parameters responsive to user input of the operational parameters or the determined operational parameters.

In an embodiment, the method 900 can further include selecting the sample type via the user interface, and wherein applying the voltage includes applying the voltage after a selected or predetermined time at least partially based on the sample or type thereof. In an embodiment, the method 900 can further include visually detecting the presence of the analyte or lack thereof. Visually detecting the presence of the analyte or lack thereof can be accomplished through a window in the housing of the flow assay or through one or more transparent electrodes or electrically conductive layer thereon, through which the at least one hydrophilic porous layer is visible or viewable. In an embodiment, a user can time keep track of the time the sample dwells at the gap before directing the application of voltage.

WORKING EXAMPLE

A working example of a flow assay was made using nitrocellulose paper as a hydrophilic porous layer, with the nitrocellulose paper having a gap filled with air therein. The nitrocellulose paper was bordered (e.g., sandwiched) by a layer of hydrophobic trichloro(perfluorooctyl)silane extending past each side of the gap. Each layer of trichloro (perfluorooctyl)silane was electrically connected to a layer of transparent indium tin oxide disposed thereon. The transparent indium tin oxide was connected to a 9 volt power source.

A potassium chloride salt solution was applied to the nitrocellulose paper. The solution progressed through the nitrocellulose paper to the gap therein. The solution did not progress past the gap. The solution stayed at the gap without progressing for more than 10 minutes. A voltage of about 9V (DC) was applied across the electrodes. Upon application of the voltage, the solution progressed across the gap and on toward the proximal end of the flow assay. Once the solution crossed the gap the application of voltage was discontinued and the progression of the solution continued.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A flow assay for detecting a presence of an analyte in a sample, the flow assay comprising:
    at least one hydrophilic porous layer having a proximal end through which the sample can be introduced, a distal end spaced from the proximal end, a first side spaced from a second side, and a gap located between the proximal end and the distal end and located between the first side and the second side;

at least one first hydrophobic layer disposed adjacent to the first side of the at least one hydrophilic porous layer to partially define the gap;

at least one second hydrophobic layer disposed adjacent to the second side of the at least one hydrophilic porous layer to partially define the gap;

a first electrode electrically coupled to the at least one first hydrophobic layer and separated from the at least one hydrophilic porous layer by the at least one first hydrophobic layer;

a second electrode electrically coupled to the at least one second hydrophobic layer and separated from the at least one hydrophilic porous layer by the at least one second hydrophobic layer; and a power source electrically coupled to the first and second electrodes, the power source configured to generate a voltage between the first electrode and the second electrode to enable at least the analyte to flow across the gap of the at least one hydrophilic porous layer.

2. The flow assay of claim 1, wherein the at least one hydrophilic porous layer includes paper.

3. The flow assay of claim 1, wherein the at least one hydrophilic porous layer includes nitrocellulose paper.

4. The flow assay of claim 1, wherein the at least one hydrophilic porous layer includes glass fibers.

5. The flow assay of claim 1, wherein each of the at least one first and at least one second hydrophobic layers includes trichloro(perfluorooctyl)silane.

6. The flow assay of claim 1, wherein the at least one first hydrophobic layer and the at least one second hydrophobic layer are made from the same type of material.

7. The flow assay of claim 1, wherein the at least one first hydrophobic layer and the at least one second hydrophobic layer are made from different types of materials.

8. The flow assay of claim 1, wherein each of the first electrode and second electrode includes a metallic film.

9. The flow assay of claim 1, wherein one or more of the first electrode or second electrode includes indium tin oxide.

10. The flow assay of claim 1, wherein one or more the first electrode or second electrode includes an electrically conductive layer through which the at least one hydrophilic porous layer is viewable therethrough.

11. The flow assay of claim 1, wherein the gap is occupied by air.

12. The flow assay of claim 1, further comprising a hydrophobic porous material disposed in the gap.

13. The flow assay of claim 12, wherein the hydrophobic porous material is a different type of material than used in each of the at least one first hydrophobic layer and the at least one second hydrophobic layer.

14. The flow assay of claim 1, wherein the at least one hydrophilic porous layer includes at least two hydrophilic porous segments spaced from each other by the gap.

15. The flow assay of claim 1, further comprising: at least one insulating layer disposed between one of the first or second electrodes and the corresponding one of the at least one first hydrophobic layer or the at least one second hydrophobic layer.

16. The flow assay of claim 15, wherein the at least one insulating layer includes polyethylene terephthalate.

17. The flow assay of claim 15, wherein the at least one insulating layer includes biaxially-oriented polyethylene terephthalate.

18. The flow assay of claim 1, wherein the power source is configured to selectively provide at least 9 V between the first electrode and the second electrode.

19. The flow assay of claim 18, wherein the power source includes a battery.

20. The flow assay of claim 1, wherein at least one of the first electrode, the second electrode, the first hydrophobic layer, or the second hydrophobic layer is configured to chemically react with the sample during application of voltage between the first electrode and the second electrode.

21. The flow assay of claim 20 wherein the at least one of the first electrode, the second electrode, the first hydrophobic layer, or the second hydrophobic layer configured to chemically react with the sample during application of voltage is configured to be coated with a product of the chemical reaction, the product of the chemical reaction being at least partially hydrophilic or less hydrophobic that the first electrode, the second electrode, the first hydrophobic layer, or the second hydrophobic layer.

22. The flow assay of claim 1, wherein at least one of the first electrode or second electrode is configured to undergo a redox reaction with the sample in the fluid during application of voltage between the first electrode and the second electrode.

23. The flow assay of claim 1, wherein the at least one hydrophilic porous layer, the at least one first hydrophobic layer, the at least one second hydrophobic layer, the first electrode, and the second electrode collectively define a lateral flow assay.

24. The flow assay of claim 1, wherein the at least one hydrophilic porous layer includes a conjugate selected to chemically react with the analyte.

25. The flow assay of claim 1, further comprising: a control system including control electrical circuitry configured to activate the power source after a selected time period, responsive to receiving an activation signal.

26. The flow assay of claim 25, wherein the selected time period is programmed into the control electrical circuitry.

27. The flow assay of claim 25, wherein the control system includes a user interface through which the activation signal can be directed to be transmitted to the control electrical circuitry.

28. The flow assay of claim 25, wherein the control system includes a user interface through which the selected time period can be selected.

29. The flow assay of claim 25, wherein the control system includes a user interface through which a sample type to be analyzed is selected, and wherein the control electrical circuitry is configured to determine the selected time period based on the selected sample type.

30. The flow assay of claim 1, further comprising: a housing at least partially enclosing at least a portion of one or more of at least one hydrophilic porous layer, the at least one first hydrophobic layer, the at least one second hydrophobic layer, the first electrode, the second electrode, or the power source.

31. The flow assay of claim 30, wherein the housing includes one or more portions through which at least a portion of the contents of the housing are visible therethrough.

32. The flow assay of claim 31 wherein the one or more portions include a transparent material.

33. The flow assay of claim 30, further comprising: a control system including control electrical circuitry configured to activate the power source after a selected time period, responsive to receiving an activation signal, wherein the housing at least partially encloses the control system.

34. A method of detecting a presence of an analyte in a sample, the method comprising:
providing a flow assay including,
at least one hydrophilic porous layer having a proximal end through which the sample can be introduced, a distal end spaced from the proximal end, a first side spaced from a second side, and a gap located between the proximal end and the distal end and located between the first side and the second side;
at least one first hydrophobic layer disposed adjacent to the first side of the at least one hydrophilic porous layer to partially define the gap;
at least one second hydrophobic layer disposed adjacent to the second side of the at least one hydrophilic porous layer to partially define the gap;
a first electrode electrically coupled to the at least one first hydrophobic layer and separated from the at least one hydrophilic porous layer by the at least one first hydrophobic layer;
a second electrode electrically coupled to the at least one second hydrophobic layer and separated from the at least one hydrophilic porous layer by the at least one second hydrophobic layer;
a power source electrically coupled to the first and second electrodes;
introducing the sample at the proximal end of the at least one hydrophilic porous layer of the flow assay; and
applying a voltage between the first electrode and the second electrode effective to alter a hydrophobicity of at least one of the at least one first hydrophobic layer or the at least one second hydrophobic layer.

35. The method of claim 34, wherein applying a voltage between the first electrode and the second electrode effective to alter a hydrophobicity of at least one of the at least one first hydrophobic layer or the at least one second hydrophobic layer includes applying the voltage to enable at least the analyte to flow across the gap in the at least one hydrophilic porous layer of the flow assay.

36. The method of claim 34, wherein applying a voltage between the first electrode and the second electrode effective to alter a hydrophobicity of at least one of the at least one first hydrophobic layer or the at least one second hydrophobic layer includes applying the voltage to enable a chemical reaction between the sample and at least one of the first electrode, the second electrode, the at least one first hydrophobic layer, or the at least one second hydrophobic layer sufficient to form a reaction product on the surface of the at least one of the first electrode, the second electrode, the at least one first hydrophobic layer, or the at least one second hydrophobic layer, wherein the reaction product is at least partially hydrophilic or less hydrophobic than the at least one of the first electrode, the second electrode, the at least one first hydrophobic layer, or the at least one second hydrophobic layer.

37. The method of claim 35, wherein applying a voltage between the first electrode and the second electrode effective to enable at least the analyte to flow across the gap in the at least one hydrophilic porous layer of the flow assay includes selectively applying the voltage after a predetermined time period at least partially based on at least one of type of the analyte, sample type, type of hydrophilic porous from which the at least one hydrophilic porous layer is made, or length of the at least one hydrophilic porous layer.

38. The method of claim 35, wherein applying a voltage between the first electrode and the second electrode effective to enable at least the analyte to flow across the gap in the at least one hydrophilic porous layer of the flow assay includes selectively applying an amount of voltage at least partially based on at least one of type of the analyte, sample type, type of hydrophilic porous material from which the at least one hydrophilic porous layer is made, length of the at least one hydrophilic porous layer, or length of time the voltage is applied.

39. The method of claim 34, further comprising: allowing the sample to flow to the gap for a predetermined amount of time prior to applying the voltage.

40. The method of claim 39, wherein the predetermined amount of time is selected so that the analyte reacts with a conjugate in the at least one hydrophilic porous layer.

41. The method of claim 34, further comprising: selecting a hydrophilic porous material from which the at least one hydrophilic porous layer is made at least partially based on at least one of type of the analyte, sample type, length of the gap, presence and type of material in the gap, or length of the at least one hydrophilic porous layer.

42. The method of claim 34, wherein:
the flow assay includes a control system having control electrical circuitry configured to control application of voltage between the first electrode and the second electrode, responsive to receiving an activation signal; and
the control system includes a user interface through which at least one of the activation signal can be directed to be transmitted to the control electrical circuitry, a selected time period after which the control electrical circuitry directs application of voltage, or the sample type is input.

43. The method of claim 42, further comprising:
inputting one or more operational parameters into the user interface at least partially based upon at least one of the type of analyte being detected, sample type, a length of the at least one hydrophilic porous layer, length of the gap, presence and type of material in the gap, type of hydrophobic material used in the at least one first and second hydrophobic layers; and
wherein responsive to the one or more operational parameters, with the control electrical circuitry, directing at least one of amount of the voltage, duration of the application of the voltage, or the selected time period.

44. The method of claim 43, wherein the one or more operational parameters include at least one of the amount of the voltage, the duration of the application of the voltage, or the selected time period.

45. The method of claim 34, further comprising:
selecting the sample type via a user interface; and
wherein applying a voltage includes applying the voltage after a selected time period at least partially based on the sample type.

46. The method of claim 34, wherein the flow assay includes a hydrophobic material disposed in the gap.

47. The method of claim 34, wherein the flow assay includes air disposed in the gap.

48. The method of claim 34, further comprising:
wherein each of the first electrode and second electrode includes an electrically conductive layer through which the at least one hydrophilic porous layer is viewable therethrough; and
visually detecting a presence of the analyte through at least one of the first electrode or the second electrode.

49. A lateral flow assay for detecting a presence of an analyte in a sample, the flow assay comprising:
at least one hydrophilic porous layer, the at least one hydrophilic porous layer having a proximal end through which the sample can be introduced, a distal end spaced from the proximal end, a first side spaced from a second side, and a gap located between the proximal end and the distal end and located between the first side and the second side;
at least one first hydrophobic layer disposed adjacent to the first side of the at least one hydrophilic porous layer to partially define the gap;
at least one second hydrophobic layer disposed adjacent to the second side of the at least one hydrophilic porous layer to partially define the gap;
a first electrode electrically coupled to the at least one first hydrophobic layer and separated from the at least one hydrophilic porous layer by the at least one first hydrophobic layer;
a second electrode electrically coupled to the at least one second hydrophobic layer and separated from the at least one hydrophilic porous layer by the at least one second hydrophobic layer;
a power source electrically coupled to the first and second electrodes, the power source configured to generate a voltage between the first electrode and the second electrode to enable at least the analyte to flow across the gap of the at least one hydrophilic porous layer; and
a control system including control electrical circuitry configured to activate the power source after a selected time period, responsive to receiving an activation signal.

50. The flow assay of claim 49, wherein the at least one hydrophilic porous layer includes paper.

51. The flow assay of claim 49, wherein the at least one hydrophilic porous layer includes nitrocellulose paper.

52. The flow assay of claim 49, wherein the at least one hydrophilic porous layer includes a glass fiber layer.

53. The lateral flow assay of claim 49, wherein the control system includes a user interface through which the selected time period can be chosen and the activation signal can be directed to be transmitted to the control electrical circuitry responsive to the selected time period being chosen.

54. The lateral flow assay of claim 49, wherein the control system includes a user interface through which the sample type is selected, and wherein the control electrical circuitry is configured to determine the selected time period based on the selected sample type.

55. The lateral flow assay of claim 49, further comprising: a hydrophobic porous material disposed in the gap.

56. The flow assay of claim 49, wherein the at least one of the first electrode, second electrode, the at least one first hydrophobic layer, or the at least one second hydrophobic layer are configured to chemically react with the sample during application of voltage, and wherein a product of the chemical reaction coats at least a portion of the at least one of the first electrode, second electrode, the at least one first hydrophobic layer, or the at least one second hydrophobic layer and wherein the product of the chemical reaction is least partially hydrophilic or less hydrophobic than the at least one of the first electrode, the second electrode, the at least one first hydrophobic layer, or the at least one second hydrophobic layer.

* * * * *